United States Patent [19]
Weber

[11] Patent Number: 5,719,277
[45] Date of Patent: Feb. 17, 1998

[54] DIAMINE SALTS OF CLAVULANIC ACID

[75] Inventor: Pieter G. Weber, Ridderkerk, Netherlands

[73] Assignee: Gist-Brocades N.V., Netherlands

[21] Appl. No.: 457,985

[22] Filed: Jun. 1, 1995

Related U.S. Application Data

[62] Division of Ser. No. 38,130, Mar. 26, 1993.

[51] Int. Cl.$^6$ .................... C07B 63/02; C07D 498/047
[52] U.S. Cl. ............................................................. 540/349
[58] Field of Search ........................................... 540/349

[56] References Cited

U.S. PATENT DOCUMENTS 5,310,898  5/1994  Copar ........................................ 540/349

FOREIGN PATENT DOCUMENTS 387178   9/1990   European Pat. Off. ............... 540/349
2517316  10/1975  Germany ................................ 540/349

*Primary Examiner*—Mark L. Berch
*Attorney, Agent, or Firm*—Bierman, Muserlian and Lucas LLP

[57] ABSTRACT

New diamine mono and diamine di salts of clavulanic acid, pharmaceutical compositions comprising the same, and a new process using these diamine salts in the preparation of clavulanic acid and salts and esters thereof have been provided.

3 Claims, No Drawings

DIAMINE SALTS OF CLAVULANIC ACID

PRIOR APPLICATIONS

This application is a division of U.S. patent application Ser. No. 038,130 filed Mar. 26, 1993.

The present invention relates to new salts of clavulanic acid, pharmaceutical compositions thereof, and to the use of these salts in the production of clavulanic acid and salts and esters thereof.

Belgian patent No. 827926 discloses that clavulanic acid, which has the formula (I):

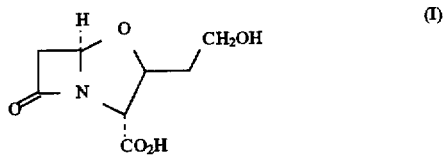

and its pharmaceutically acceptable salts and esters are anti-bacterial agents, able to enhance the effectiveness of penicillins and cephalosporins against many β-lactamase-producing bacteria.

In U.S. Pat. No. 4,650,795 a defined group of primary amine salts of clavulanic acid has been disclosed to give stable pharmaceutical compositions.

EP patent 26044 discloses the use of one of such an amine salt, viz. the t-butylamine salt as an useful intermediate in the preparation of clavulanic acid.

Surprisingly it was found that a defined group of diamine mono salts and diamine di salts of clavulanic acid, viz. the tertiary, tertiary diamine salts, have properties more superior compared to the t-butyl amine salt of clavulanic ester mentioned above. For instance, the big crystals of the mono salt of N,N,N',N'-tetramethyl-1,2-diaminoethane clavulanate can easily be precipitated in pure form making the same a very useful intermediate in the preparation of clavulanic acid.

Accordingly, the present invention provides tertiary, tertiary diamine mono salts of the formula (IIa):

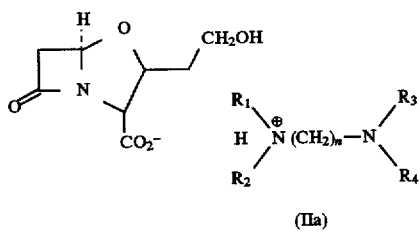

and tertiary, tertiary diamine di salts of formula (IIb):

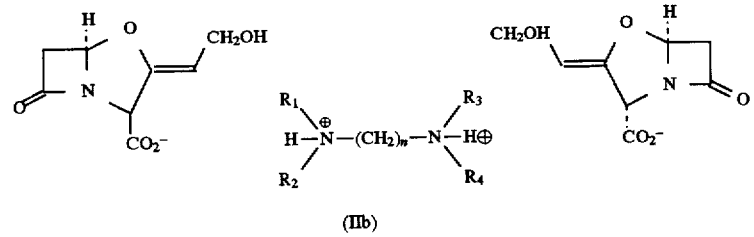

$R_1$ and $R_2$ are optionally inertly substituted (1–8C)alkyl, (3–8C)cycloalkyl or (3–8C)cycloalkyl (1–8C)alkyl, or $R_1$ and $R_2$ are interlinked to form a ring of 4–7 ring atoms; $R_3$ and $R_4$ are optionally inertly substituted (1–8C)alkyl, (3–8C)cycloalkyl or (3–8C)cycloalkyl(1–8C)alkyl, or $R_3$ and $R_4$ are interlinked to form a ring of 4–7 atoms; and n=1–10.

The present invention also provides a process for the preparation of a salt of formulae (IIa) or (IIb) which process comprises the reaction of clavulanic acid with diamine (III):

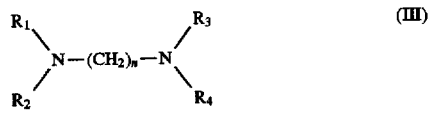

where the diamine mono clavulanate will be formed at a relatively high amount of diamine compared to clavulanic acid and the diamine di clavulanate will be formed at a relatively low amount of diamine compared to clavulanic acid or a mixture of the same at a concentration in between. The difference in concentration may, for instance, be obtained by varying the pH whereby at relatively high pH (dependent on the amine and the solvent used) more mono-protonated diamine (IIIa):

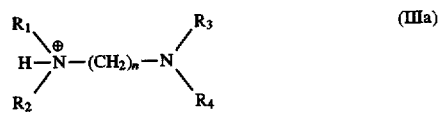

will be present and therefore more mono salt will be precipitated, and at relatively low pH more di-protonated diamine (IIIb):

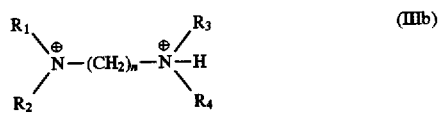

will be present and therefore more di salt will be precipitated.

The present invention further provides the use of diamine mono and diamine di salts of clavulanic acid as defined above as an intermediate in the preparation of clavulanic acid and a pharmaceutically acceptable salt or ester thereof.

In another aspect the present invention provides a process for the preparation of clavulanic acid or a pharmaceutically acceptable salt or ester thereof which process comprises converting a diamine mono or diamine di salt of clavulanic acid as defined above into clavulanic acid or a pharmaceutically acceptable salt or ester thereof.

In a further aspect the present invention provides a process for the purification of clavulanic acid or a pharmaceutically acceptable salt or ester thereof which process comprises:

i) contacting impure clavulanic acid in an organic solvent with diamine;

ii) isolating the diamine mono or diamine di salt of clavulanic acid; and iii) converting the thus formed diamine clavulanate in clavulanic acid or a pharmaceutically acceptable salt or ester thereof.

Suitable inert substituents include halogen, hydroxy, lower alkoxyl, lower acyloxyl, lower esterified carboxyl and the like groups. Suitably 1, 2 or 3 such substituent groups are present, more suitably 1 or 2 and preferably not more than one such substituent group is present.

Normally the amine of the formula (III):

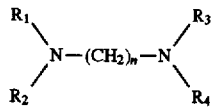

from which the salts of the formulae (IIa) and (IIb) are derivable is a pharmaceutically acceptable amine.

Suitably both $R_1$, $R_2$, $R_3$ and $R_4$ groups are each independently (1–8C)alkyl or $R_1$ and $R_2$ or $R_3$ and $R_4$ are each independently interlinked to form a ring of 4–7 atoms, preferably a saturated one.

Preferably, the salts of the formulae (IIa) and (IIb) are derivable from N,N,N',N'-tetramethyl-1,2-diaminoethane, N,N,N',N'-tetramethyl-1,4-diaminobutane, N,N,N',N'-tetramethyl-1,6-diaminohexane, 1,2-dipiperidinoethane and dipiperidinomethane.

Most suitably the formation of the diamine salts of clavulanic acid takes place in an organic solvent. Suitable solvents include such conventional non-hydroxylic solvents as tetrahydrofuran, dioxane, ethyl acetate, methyl acetate, acetone, methylethylketone and the like solvent and mixtures thereof.

This reaction may take place at any non-extreme temperature but in general temperatures of from 0° C. to 50° C. are most suitable and temperatures of from 5° C. to 35° C. are generally most convenient.

The present invention also provides pharmaceutical compositions which comprise a salt of the formulae (IIa) and/or (IIb) and a pharmaceutically acceptable carrier.

Suitable forms of the compositions of this invention include tablets, capsules, reconstitutable powders and sterile forms suitable for injection or infusion. Such compositions may contain conventional pharmaceutically acceptable materials such as diluents, binders, colours, flavours, preservatives, disintegrants and the like in accordance with conventional pharmaceutical practice in the manner well understood by those skilled in the art of formulating antibiotics.

Injectable or infusable compositions of the salts of formulae (IIa) and (IIb) are particularly suitable as high tissue levels of the compound of clavulanic acid can occur after administration by injection or infusion. Thus, one preferred composition aspect of this invention comprises salts of the formulae (IIa) and (IIb) in sterile form.

Unit dose compositions comprising a salt of the formula (II) adapted for oral administration form a further preferred composition aspect of this invention.

The following examples will illustrate the invention.

EXAMPLES

Example 1

Comparison of Crystallization of Various Diamine Salts

A solution of potassium clavulanate in ice cold water was stirred with ethyl acetate under cooling with ice-water. With a solution of about 10% (w/w) sulphuric acid the pH was brought at about 2, the water layer separated and two times extracted with ethyl acetate. The collected extracts were dried with magnesium sulphate, filtered and washed with ethyl acetate, yielding a solution of clavulanic acid of about 2% (w/w).

After a 1:1 dilution of this solution with acetone diamine was added. The results have been summarized in Table I.

TABLE I

| Diamine | type* | crystals | oil | diamine** |
|---|---|---|---|---|
| N,N,N',N'-tetramethyl-1,2-diaminoethane | t,t | + | – | 1.90 |
| N,N,N',N'-tetramethyl-1,2-diaminoethane | t,t | + | – | 0.68 |
| N,N,N',N'-tetramethyl-1,3-diaminopropane | t,t | + | – | 1.89 |
| N,N,N',N'-tetramethyl-1,4-diaminobutane | t,t | + | – | 1.34 |
| N,N,N',N'-tetramethyl-1,6-diaminohexane | t,t | + | – | 1.84 |
| 1,2-dipiperidinoethane | t,t | + | – | 2.70 |
| dipiperidinomethane | t,t | + | – | 14.92 |
| 1,2-diaminoethane | p,p | + | + | 3.98 |
| 1,3-diaminopropane | p,p | + | + | 1.69 |
| 1,6-diaminohexane | p,p | – | + | 1.69 |
| 1,10-diaminodecane | p,p | – | + | 1.46 |
| N-methyl-1,3-diaminopropane | p,s | – | + | 1.69 |
| N,N-dimethyl-1,3-diaminopropane | p,t | – | + | 1.86 |
| N,N-dimethyl-1,2-diaminoethane | p,t | – | + | 1.69 |
| piperazine | s,s | – | + | 1.20 |
| N-methylpiperazine | s,t | – | + | 1.20 |
| N,N-diethyl-1,2-diaminoethane | p,t | – | – | 0.81 |
| N-(2-aminoethyl)-morfoline | p,t | – | – | 1.20 |

*p: primary; s: secondary; t: tertiary
**moles diamine/clavulanic acid

Example 2

Preparation of N,N,N',N'-tetramethylethylene diamine mono clavulanate from ethylacetate/acetone A clavulanic acid extract in dry ethyl acetate (828 g containing 18 g of clavulanic acid/kg prepared according to example 1) was added in 20 min to 1 l of acetone while cooling (8° C.) and keeping the pH at 9 with N,N,N',N'-tetramethylethylene diamine (TMEDA, 19.18 g, 2.2 Mol). Stirring was continued at 10° C. for 1 hr. The precipitate was filtered off and washed with 100 ml or acetone and dried in vacuum at 35° C. to yield 20.09 g of TMEDA mono clavulanate (big crystals). The mother liquor (1642 g) contained about 1.12 g of clavulanic acid.

NMR (DMSO-d6): 2.37 ppm, N—$CH_3$ (s, 12H); 2.70 ppm, N—$CH_2$ (s, 4H); 2.95 ppm, C6-βH (d, 1H); 3.49 ppm, C6-αH (dd, 1H); 3.99 ppm, $CH_2OH$ (m, 2H); 4.60 ppm, C3-H (s, 1H); 4.66 ppm, =C—H (tr, 1H); 5.58 ppm, C5-H (d, 1H).

Example 3

Preparation of N,N,N',N'-tetramethyl-1,2-diaminoethane mono clavulanate from ethylacetate A solution of clavulanic acid in ethyl acetate (75 g, containing about 20 g of clavulanic acid/kg) was added in 10 min to 75 ml of ethyl acetate at 8° C. while stirring and keeping the pH between 8 and 9 with N,N,N',N'- tetramethylethylene diamine (TMEDA, 5.11 g, 8 Mol). Stirring was continued for 0.5 hr and the precipitate was filtered off, washed with ethyl acetate and dried in vacuum at 35° C. to give 2.62 g of TMEDA mono clavulanate (big crystals). The mother liquor (155 g) contained 0.03 g of clavulanic acid.

NMR (DMSO-d6): 2.38 ppm, N—$CH_3$ (s, 12H); 2.70 ppm, N—$CH_2$ (s, 4H); 2.93 ppm, C6-βH (d, 1H); 3.48 ppm, C6-αH (dd, 1H), 3.98 ppm, $CH_2OH$ (m, 2H); 4.58 ppm, C3-H (s, 1H); 4.65 ppm, =C—H (tr, 1H); 5.58 ppm, C5-H (d, 1H).

Example 4

Preparation of N,N,N',N'-tetramethyl-1,2-diaminoethane di clavulanate from ethylacetate/acetone A solution of clavulanic acid in ethyl acetate (200 ml containing 1.1 g of clavulanic acid) was added in 10 min to 200 ml of cold acetone (10° C.) while stirring and keeping the pH between 7.5 and 8 with N,N,N',N'-tetramethylethylene diamine (TMEDA, 0.64 g, 1.45 Mol). Stirring was continued for 0.5 hr and the precipitate was filtered off, washed with acetone and dried in vacuum at 35° C. to give 1.24 g of TMEDA di clavulanate (crystals in needle form). The mother liquor (337 g) contained 0.11 g of clavulanic acid.

NMR (DMSO d6): 2.45 ppm, N—$CH_3$ (s, 12H); 2.80 ppm, N—$CH_2$ (s, 4H); 2.99 ppm, C6-βH (d, 2H); 3.53 ppm, C6-αH (dd, 2H; 3.99 ppm, $CH_2OH$ (m, 4H); 4.69 ppm, =C—H (tr, 2H); 4.76 ppm, C3-H (s, 2H); 5.61 ppm, C5-H (d, 2H).

Example 5

Conversion of N,N,N',N'-tetramethyl-1,2-diaminoethane mono clavulanate in potassium clavulanate 30 ml of a 0.35M potassium acetate solution (solvent isopropylalcohol and 1% (w/v) water) was added dropwise to a suspension of 2 g of N,N,N',N'-tetramethyl-1,2-diammonium mono clavulanate (content 68.6%) in 50 ml of isopropanol. After still 0.75 hr stirring at room temparature of the precipitate was filtered, washed with 10 ml of isopropanol and dried in vacuum at 35° C. yielding 1.44 g of crystalline potassium clavulanate with a content of 87% (clavulanic acid) and about 1.5% potassium acetate (HPLC analysis). The mother liquor contained about 0.06 g of clavulanic acid.

I claim:

1. A salt of clavulanic acid of the formula (IIa):

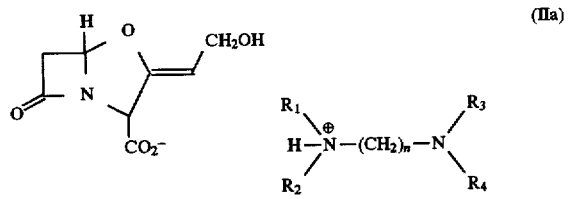

(IIa)

wherein $R_1$, $R_2$, $R_3$ and $R_4$ are individually selected from the group consisting of alkyl of 1 to 8 carbon atoms, cycloalkyl of 3 to 8 carbon atoms and cycloalkyl alkyl of 3 to 8 cycloalkyl carbon atoms and alkyl of 1 to 8 carbon atoms, all optionally substituted with 1 to 3 members of the group consisting of halogen, —OH, lower alkoxy and carboxy esterified with lower alkyl or $R_1$ and $R_2$ or $R_3$ and $R_4$ taken with the nitrogen to which they are attached form piperidino; and n is an integer from 1 to 10.

2. A pharmaceutical composition comprising a diamine mono salt of clavulanic acid as defined in claim 1 and a pharmaceutical carrier.

3. A diamine mono salt of clavulanic acid according to claim 1 where $R_1$, $R_2$, $R_3$ and $R_4$ are methyl, and n=2.

* * * * *